United States Patent [19]
Morellet et al.

[11] Patent Number: 4,588,841
[45] Date of Patent: May 13, 1986

[54] PROCESS FOR THE PREPARATION OF AMINOPHENOLS

[75] Inventors: Guy Morellet; Jean-Claude Jacquesy; Marie-Paule Jouannetaud, all of Poitiers, France

[73] Assignee: Atochem, France

[21] Appl. No.: 620,033

[22] Filed: Jun. 13, 1984

[30] Foreign Application Priority Data

Jun. 29, 1983 [FR] France ................. 83 10730

[51] Int. Cl.⁴ ........................................... C07C 91/42
[52] U.S. Cl. ............................................... 564/443
[58] Field of Search ..................................... 564/443

[56] References Cited

FOREIGN PATENT DOCUMENTS 3102305  8/1982  Fed. Rep. of Germany .

OTHER PUBLICATIONS

Jacquesy et al., *Tetrahedron Letters*, vol. 25, No. 14, pp. 1479–1482, 4/1984.

Primary Examiner—Charles F. Warren
Assistant Examiner—Elizabeth A. Flaherty
Attorney, Agent, or Firm—Sigalos & Levine

[57]     ABSTRACT

Process for the preparation of aminophenols with an increased proportion of the meta isomer comprising reacting hydrogen peroxide in a superacid liquid medium with anilines, N-alkylaniline, or N,N-dialkylanilines for a time and a temperature, ranging from about −50° C. to 0° C., sufficient to form the aminophenols.

5 Claims, No Drawings

PROCESS FOR THE PREPARATION OF AMINOPHENOLS

BACKGROUND OF THE INVENTION

The present invention concerns a process for the preparation of aminophenols by the hydroxylation, in liquid superacid medium utilizing hydrogen peroxide, of certain aromatic amines.

The invention allows the introduction of a phenol function on the aromatic ring of the amine in the ortho, meta, and para positions in relation to the amine group, without oxidation of the nitrogen of the amine functional group. The proportion of the meta-aminophenol formed is predominant.

French Pat. No. 82 10644 describes a process for the hydroxylation of anilides; i.e., amides derived from aniline, with hydrogen peroxide in a superacid medium. It is particularly surprising that an analogous process can be applied to unprotected anilines, since prior art very clearly teaches that peroxide compounds (hydrogen peroxide, organic peracids, hydroperoxides, diacyl peroxides) in general attack the nitrogen of the amine function with the formation of hydroxylamine, amine oxide, nitroso derivatives, azo derivatives, azoxy derivatives or polymers. Sometimes an attack on the alkyl groups borne by the nitrogen of secondary and tertiary aromatic amines is observed involving dealkylation reactions or the formation of imines.

These different modes of action of peroxide compounds on aromatic amines are described in the following references:

B. C. CHALLIS and A. R. BUTLER, in "The Chemistry of the Amino Group" (PATAI), p. 320–338, Interscience Publishers, New York, 1968;

M. HEDAYATULLAH, *Bull. Soc. Chim. France*, 1972, p. 2957–2974; and

J. P. SCHIRMANN and S. Y. DELAVARENNE, "Hydrogen Peroxide in Organic Chemistry", chapter VII, p. 147–156, EDI Paris, 1979.

In the special case of N,N-dialkylanilines, oxidation by peroxydisulfate ions, known under the name of BOYLAND-SIMS reaction, leads to the introduction on the aromatic ring of a sulfate group, later hydrolyzable into a phenol group. This introduction essentially takes place in the ortho position with respect to the amine group, with the para isomer forming in significant proportions only when the two ortho positions are blocked. No meta isomer is formed. This BOYLAND-SIMS reaction has been studied by E. J. BEHRMAN and D. M. BEHRMAN, *J. Org. Chem.*, 43, No. 23, p. 4551–4552 (1978).

SUMMARY OF THE INVENTION

It has now been surprisingly found that aminophenols can be prepared without attack on the amino nitrogen to form undesired products, such as imines.

Briefly stated, the present invention comprises a process for the preparation of aminophenols with an increased proportion of the meta isomer thereof comprising reacting hydrogen peroxide in a superacid liquid medium with an aromatic amine of the formula:

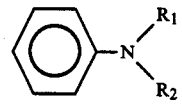

in which $R_1$ and $R_2$ represent either hydrogen atoms, or a $C_1$-$C_8$ alkyl radical at a temperature of from about $-50°$ C. to $0°$ C. for a time sufficient to form the aminophenols.

DETAILED DESCRIPTION

According to the present invention, the hydroxylation on the aromatic ring of free amines, yielding large proportions of meta isomers, is achieved by causing hydrogen peroxide to act at low temperatures on the desired amine in a liquid superacid medium.

This liquid superacid medium consists of products which, on HAMMETT's logarithmic scale, have acidities reaching about $-25$. By way of comparison, 100% sulfuric acid has an acidity of $-11$ and anhydrous hydrofluoric acid has an acidicity of $-10$. The liquid superacids used thus have acidities up to $10^{14}$ times higher than those of the customary strong mineral acids. Examples of liquid superacids utilizable in the process of the invention are "magic acid" $FSO_3H$-$SbF_5$, fluoroantimonic acid $HF$-$SbF_5$, the complexes of trifluoromethane sulfonic acid with antimony pentafluoride $CF_3SO_3H$-$SbF_5$, and the complex of hydrofluoric acid with boron trifluoride $HF$-$BF_3$.

The hydrogen peroxide is utilized in the form of commercial aqueous solutions, whose titer can go from 20% to 98% by weight. The commercial solution of 70% by weight of $H_2O_2$ is preferably used. The molar ratio of hydrogen peroxide to the substrate to be hydroxylated is generally between 1 and 2.

The proportion of superacid in relation to the aromatic amine can vary within wide limits. Generally, the proportion of superacid increases with the degree of dilution of the aqueous solution of the hydrogen peroxide. With a 70% solution of hydrogen peroxide by weight, from 4 to 20 milliliters of superacid per millimole of substrate are customarily used.

The reaction proceeds at temperatures from about $-50°$ C. to about $0°$ C., at atmospheric pressure or under pressures exceeding atmospheric pressure, especially when the $HF$-$BF_3$ complexes are used. The duration of the reaction is from several minutes to one hour.

The general operating method followed in order to implement the process of the invention is very simple; the liquid superacid, the aromatic amine, and the hydrogen peroxide are successively introduced into a container made of poly(tetrafluoroethylene), or of stainless steel when operating with the $HF$-$BF_3$ complexes, equipped with a magnetic agitation apparatus and cooled to the desired temperature. The mixture is kept under agitation for the desired time at the selected temperature. It is then poured on a mixture of water, ice, and sodium bicarbonate. After neutralization, the solution is extracted several times with a low molecular weight organic solvent, such as diethyl ether. After evaporation of the solvent of extraction, the crude product is chromatographed on a silica gel by using as the eluent an organic solvent or a mixture of organic solvents making possible the separation of the reaction products.

According to a variation of this general operating method, one can introduce the hydrogen peroxide into the superacid prior to the substrate to be hydroxylated. According to other variations suitable especially for the HF-BF$_3$ mixtures, one introduces into the reactor first the substrate, then the superacid and the hydrogen peroxide, or the substrate, then the hydrogen peroxide and the superacid.

The invention will be further illustrated in conjunction with the following examples, which are set forth for purposes of illustration only and not by way of limitation.

EXAMPLE 1

Example 1 exemplifies the hydroxylation of aniline in HF-SbF$_5$ medium.

(a) According to the general operating method, a mixture of 17.5 ml of anhydrous hydrofluoric acid and 2.5 ml of antimony pentafluoride (molar ratio of SbF$_5$/HF=0.04) is cooled to −40° C. To this mixture 4 millimoles of aniline are successively added and 4 millimoles of hydrogen peroxide in the form of a 70% aqueous solution by weight. The reaction mixture is kept under agitation for 15 minutes at −40° C.

After treatment, the crude product obtained, weighing 320 mg, is chromatographed on a silica gel under nitrogen pressure. A 50/50 mixture by volume of hexane and ethyl acetate successively elutes the unconverted aniline, 2-aminophenol, 3-aminophenol, and 4-aminophenol. The structure of the products formed is determined by physical and spectroscopic characteristics (nuclear magnetic resonance, infrared, and mass spectrum) and also from identification with known products.

(b) The above test is repeated, but at a temperature of −20° C. and by using a molar ratio of H$_2$O$_2$/substrate of 1.5 instead of 1.0.

The quantitative results of these two tests are given in Table I.

TABLE I

| Test | Degree of Conversion of the Aniline | Yield of Aminophenols | Relative Proportions of the Isomers (Percentages) | | |
|---|---|---|---|---|---|
| | | | ortho | meta | para |
| 1a | 68% | 40% | 35 | 57 | 8 |
| 1b | 95% | 70.5% | 29 | 51 | 20 |

EXAMPLE 2

Example 2 exemplifies the hydroxylation of N,N-dimethylaniline in HF-SbF$_5$ medium with 70% hydrogen peroxide.

A mixture of 15.75 ml anhydrous hydrofluoric acid and 2.25 ml antimony pentafluoride (molar ratio of SbF$_5$/HF=0.04) is cooled to −20° C. and to this mixture 4 millimoles of N,N-dimethylaniline are successively added and 4 millimoles of hydrogen peroxide in the form of an aqueous solution of 70% by weight.

The reaction mixture is kept at −20° C. under agitation for 15 minutes. After treatment, 540 mg of crude product are obtained which are chromatographed on silica gel under nitrogen pressure. A 70/30 mixture by volume of hexane and ethyl acetate makes it possible to elute successively:

unconverted N,N-dimethylaniline (12%)
2-hydroxy N,N-dimethylaniline (14%)
3-hydroxy N,N-dimethylaniline (44%)
4-hydroxy N,N-dimethylaniline (26%)

The relative proportions of the hydroxylated isomers are:

ortho: 17%
meta: 52%
para: 31%

Since the para isomer is difficult to identify by nuclear magnetic resonance of the proton, it has been characterized by the NMR spectrum of its acetyl derivative, obtained by the action of acetic anhydride.

EXAMPLE 3

Example 3 exemplifies the hydroxylation of N,N-diethylaniline in HF/SbF$_5$ medium.

(a) To a mixture of 15.75 ml of anhydrous hydrofluoric acid and 2.25 ml of antimony pentafluoride (molar ratio of SbF$_5$/HF=0.04), cooled to −20° C., 4 millimoles of N,N-diethylaniline are successively added and 4.4 millimoles of hydrogen peroxide in the form of a 70% aqueous solution by weight. The reaction mixture is kept under agitation at −20° C. for 15 minutes.

After treatment, the crude product weighing 610 mg is chromatographed on silica gel. The 90/10 mixture by volume of hexane and diethyl ether elutes 390 mg of a mixture composed of unconverted N,N-diethylaniline (312 mg) and of 2-hydroxy-N,N-diethylaniline (78 mg). The determination of the two products present in the mixture is carried out by NMR of the proton.

The 70/30 mixture by volume of hexane and diethyl ether elutes 190 mg of a 3-hydroxy-N,N-diethylaniline.

Finally, the 60/40 mixtures by volume of hexane and diethyl ether elutes 22 mg of a mixture of two products which have not accurately been identified. However, the mass spectrum of the mixture causes a peak which corresponds to 4-hydroxy-N,N-diethylaniline.

(b) The above test is repeated, but by using a molar ratio of H$_2$O$_2$/substrate of 1.5 instead of 1.1.

In this test, the mixture of the two most polar products eluted by the 60/40 hexane/diethyl ether mixture weights 140 mg.

Table II summarizes the quantitative results of the two tests, 3a and 3b.

The yield of 4-hydroxy-N,N-diethylaniline, insufficiently identified, has not been shown.

TABLE II

| Test | Degreee of Conversion of the N,N—diethylaniline | Yields of Hydroxylated Derivatives | | |
|---|---|---|---|---|
| | | ortho | meta | para |
| 3a | 48% | 12% | 29% | — |
| 3b | 87.5% | 11% | 49% | — |

EXAMPLE 4

Example 4 exemplifies the hydroxylation of N-ethylaniline in HF-SbF$_5$ medium.

A mixture of 17.5 ml of anhydrous hydrofluoric acid and 2.5 ml of antimony pentafluoride (molar ratio of SbF$_5$/HF=0.04) is cooled to −20° C. and to this mixture 4 millimoles of N-ethylaniline are successively added and 6 millimoles of hydrogen peroxide in the form of a 70% aqueous solution by weight.

The reaction duration under agitation at −20° C. is 15 minutes.

After treatment, 520 mg of crude product are obtained which are chromatographed on silica gel.

The 85/15 mixture by volume of hexane and diethyl ether elutes 23 mg (4.5%) of N-ethylaniline not having reacted.

The 70/30 mixture by volume of hexane and diethyl ether elutes 100 mg (18%) of 2-hydroxy N-ethylaniline.

The 65/35 mixture by volume of hexane and diethyl ether elutes 221 mg (40.5%) of 3-hydroxy-N-ethylaniline.

The 55/45 mixture by volume of hexane and diethyl ether elutes 90 mg (16.5%) of 4-hydroxy-N-ethylaniline.

The relative proportions of hydroxylated isomers thus are:
ortho: 24%
meta: 54%
para: 22%

EXAMPLE 5

Example 5 exemplifies the hydroxylation of N,N-dimethylaniline in HF-SbF$_5$ medium by 35% hydrogen peroxide.

(a) To a mixture of 17.5 ml of anhydrous hydrofluoric acid and 2.5 ml of antimony pentafluoride (molar ration of SbF$_5$/HF=0.04), cooled to −20° C., 2 millimoles of N,N-dimethylaniline are successively added and 3 millimoles of hydrogen peroxide in the form of a 35% aqueous solution by weight.

After 15 minutes of reaction at −20° C. under agitation, the reaction mixture is treated in the usual manner.

240 mg of crude product are obtained, which are chromatographed on silica gel. The unconverted N,N-dimethylaniline is eluted by a 90/10 hexane/diethyl ether mixture by volume. The 2-hydroxy-N,N-dimethylaniline is eluted by an 80/20 mixture of the same solvents. The 70/30 mixture elutes the 3-hydroxy-N,N-dimethylaniline and the 55/45 mixture elutes the 4-hydroxy-N,N-dimethyl-aniline. A 45/55 mixture makes it possible to elute 15 mg of a more polar product which has not been identified.

(b) The preceding test is repeated, but by utilizing a mixture of 7.5 ml of hydrofluoric acid and 2.5 ml of antimony pentafluoride (molar ratio of SbF$_5$/HF=0.09) and by placing into the reaction 3.4 millimoles of 35% hydrogen peroxide.

After treatment, 270 mg of crude product are obtained which are chromatographed as above. The 45/55 hexane/diethyl ether mixture elutes 25 mg of an unidentified product.

Table III gives the quantitative results of tests 5a and 5b.

TABLE III

| Test | Degree of Conversion of the N,N—dimethylaniline | Yield of Dimethyl-amino-phenols | Relative Proportions of the Isomers | | |
|---|---|---|---|---|---|
| | | | ortho | meta | para |
| 5a | 54.5% | 26.5% | 11% | 60.5% | 28.5% |
| 5b | 65% | 57.5% | 12% | 63% | 25% |

EXAMPLE 6

Example 6 exemplifies the hydroxylation of N,N-dimethylaniline in CF$_3$SO$_3$H-SbF$_5$ medium.

(a) A mixture of 6 ml of trifluoromethane sulfonic acid and of 3 ml of antimony pentafluoride (molar ratio SbF$_5$/CF$_3$SO$_3$H=0.6) is homogenized at −20° C. and to this mixture 3 millimoles of hydrogen peroxide are successively added in the form of a 70% aqueous solution by weight and 2 millimoles of N,N-dimethylaniline.

The reaction mixture is kept at −20° C. under agitation for 8 minutes.

After treatment, 125 mg of crude product are obtained. Chromatography of this product, carried out as in Example 5, makes it possible to obtain 40 mg (yield 14.5%) of 3-hydroxy-N,N-dimethylaniline and 40 mg (yield 14.5%) of 4-hydroxy-N,N-dimethylaniline.

(b) The preceding test is repeated, but by introducing the amine into the superacid medium prior to the hydrogen peroxide and by raising the reaction duration to 10 minutes. 160 mg of crude product are obtained. Chromatography makes it possible to recover 28% of unconverted N,N-dimethylaniline and to isolate 48 mg (yield 17.5%) of 3-hydroxy-N,N-dimethylaniline and 20 mg (yield 7.5%) of 4-hydroxy-N,N-dimethylaniline. The 45/55 hexane/diethyl ether mixture elutes 19 mg of an unidentified more polar product.

EXAMPLE 7

Example 7 exemplifies the hydroxylation of N,N-dimethylaniline in FSO$_3$H-SbF$_5$ medium.

A mixture of 6 ml of fluorosulfuric acid and 3 ml of antimony pentafluoride (molar ratio of SbF$_5$/FSO$_3$H=0.4) is cooled to −20° C. and to this mixture 3 millimoles of hydrogen peroxide are successively added in the form of a 70% aqueous solution by weight and 2 millimoles of N,N-dimethylaniline. The reaction duration under agitation at −20° C. is 15 minutes.

After treatment, 160 mg of crude product are obtained which are filtered on silica gel. The 70/30 mixture by volume of hexane and diethyl ether elutes 62 mg (yield 22.5%) of 3-hydroxy-N,N-dimethylaniline, while the 55/45 mixture of the same solvents elutes 45 mg (yield 16.5% of 4-hydroxy-N,N-dimethylaniline. The remainder of the crude product is composed of unidentified polymer materials.

EXAMPLE 8

Example 8 exemplifies the hydroxylation of N,N-dimethylaniline in HF-BF$_3$ medium.

Into a container made of poly(tetrafluoroethylene) and cooled to −40° C., 15 ml of anhydrous hydrofluoric acid are poured, in which a stream of boron trifluoride is made to bubble for 15 minutes. Two millimoles of N,N-dimethylaniline are then added and then 2.2 millimoles of hydrogen peroxide (70% aqueous solution by weight). A stream of boron trifluoride is made to bubble again and the medium is kept under agitation at −40° C. for 20 minutes.

After treatment, 250 mg of crude product are obtained which is chromatographed on silica gel. The 85/15 mixture by volume of hexane/diethyl ether elutes the unconverted N,N-dimethylaniline (210 mg—87%). The 70/30 mixture of the same solvents elutes 16 mg (6%) of 3-hydroxy-N,N-dimethylaniline. Only less than 1% of the para-hydroxylated derivative has been formed.

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. Process for the preparation of aminophenols with an increased proportion of the meta isomer thereof comprising reacting hydrogen peroxide in a superacid liquid medium with an aromatic amine of the formula:

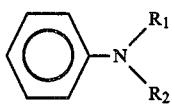

in which $R_1$ and $R_2$ represent either a hydrogen atom or a $C_1$–$C_8$ alkyl radical at a temperature of from about −50° C. to 0° C. for a time sufficient to form the aminophenols.

2. The process of claim 1, wherein the superacid liquid medium is selected from a complex of anhydrous hydrofluoric acid and antimony pentafluoride, a complex of fluorosulfonic acid and antimony pentafluoride, a complex of trifluoromethane sulfonic acid and antimony pentafluoride, or a complex of anhydrous hydrofluoric acid and boron trifluoride.

3. The process according to claim 2, wherein the hydrogen peroxide comprises an aqueous solution containing between about 20% to 98% by weight of hydrogen peroxide, preferably containing 70% by weight of hydrogen peroxide.

4. The process according to claim 3, wherein the molar ratio of the hydrogen peroxide to the aromatic amine is between 1 and 2.

5. The process according to claim 4, wherein 4 to 20 milliliters of liquid superacid are utilized per millimole of substrate to be hydroxylated.

* * * * *